(12) United States Patent
Sugiyama et al.

(10) Patent No.: US 7,588,739 B2
(45) Date of Patent: Sep. 15, 2009

(54) FIXED BED MULTITUBE REACTOR

(75) Inventors: Miezi Sugiyama, Otake (JP);
Yoshimasa Ando, Huizhou (CN);
Yoshiyuki Taniguchi, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 201 days.

(21) Appl. No.: 10/564,434

(22) PCT Filed: Jul. 13, 2004

(86) PCT No.: PCT/JP2004/010273

§ 371 (c)(1),
(2), (4) Date: Jun. 19, 2006

(87) PCT Pub. No.: WO2005/005037

PCT Pub. Date: Jan. 20, 2005

(65) Prior Publication Data

US 2007/0049769 A1 Mar. 1, 2007

(30) Foreign Application Priority Data

Jul. 14, 2003 (JP) .............................. 2003-274140

(51) Int. Cl.
*B01J 8/04* (2006.01)
*B01J 10/00* (2006.01)
*C07C 51/16* (2006.01)
*C07C 1/00* (2006.01)

(52) U.S. Cl. ........................ 422/197; 422/107; 422/198; 422/201; 422/190; 562/544; 562/545; 562/531; 562/532; 585/639; 585/640

(58) Field of Classification Search .................. 422/107, 422/197, 198, 200, 201, 190; 562/544, 545, 562/532, 531; 585/639, 640
See application file for complete search history.

(56) References Cited

U.S. PATENT DOCUMENTS

| 4,929,798 A | * | 5/1990 | de Lasa | ...................... 585/402 |
| 6,333,011 B1 | * | 12/2001 | Schliephake et al. | ......... 422/197 |
| 7,226,567 B1 | * | 6/2007 | Olbert et al. | ................. 422/197 |
| 2003/0006026 A1 | * | 1/2003 | Matsumoto et al. | ......... 165/157 |

FOREIGN PATENT DOCUMENTS

| JP | 06-192144 | | 7/1994 |
| JP | 08-92147 | | 4/1996 |
| JP | 10-309457 | | 11/1998 |
| JP | 2001-139499 | | 5/2001 |
| JP | 2002-212127 | | 7/2002 |
| JP | 2003-1094 | | 1/2003 |
| WO | WO00/17946 | * | 3/2000 |
| WO | WO 00/54877 | * | 9/2000 |

* cited by examiner

*Primary Examiner*—Walter D Griffin
*Assistant Examiner*—Lessanework Seifu
(74) *Attorney, Agent, or Firm*—Oblon, Spivak, McClelland, Maier & Neustadt, P.C.

(57) ABSTRACT

A fixed-bed multitubular reactor, comprising a plurality of reaction tubes (3) filled with a catalyst and catalyst temperature measurers (4) measuring the temperatures of the reaction tubes near the radical center parts thereof. The catalyst temperature measurer (4) is installed in each of a part of the plurality of reaction tubes (3), and the measurement positions thereof are differentiated from each other in the longitudinal direction of the reaction tubes (3).

11 Claims, 4 Drawing Sheets

FIXED BED MULTITUBE REACTOR

TECHNICAL FIELD

The present invention relates to a fixed-bed multitubular reactor in which a gas-phase catalytic oxidation reaction is performed by using a solid catalyst.

The present application claims the priority of Japanese Patent Application No. 2003-274140 filed on Jul. 14, 2003, the contents of which are incorporated herein by reference.

BACKGROUND ART

A gas-phase catalytic oxidation reaction using a solid catalyst is being performed on a commercial scale. As the gas-phase catalytic oxidation reaction, for example, a production of acrolein or acrylic acid from propylene and a production of methacrolein or methacrylic acid from isobutylene or tertiary butyl alcohol are exemplified.

These gas-phase catalytic oxidation reactions use molecular oxygen and synthesize a useful target compound by stopping a reaction at an intermediate oxidation state. For example, it is possible to synthesize acrolein from one mole of propylene and one mole of oxygen and to synthesize acrylic acid from one mole of acrolein and a half mole of oxygen.

However, in such an oxidation reaction, there occurs a decomposition reaction or an oxidation reaction simultaneously or successively as well as a reaction for obtaining a target product. As a result, a byproduct such as carbon dioxide, which is the most oxidized state, and the like may be generated in some cases.

Under these circumstances, because gas-phase catalytic oxidation reactions are complicated reactions, a manufacturing method by which a target product can be synthesized in a high yield is being investigated among such reactions.

A temperature condition with which a target product can be obtained in a high yield by stopping an oxidation reaction at an intermediate stage is in a narrow range. Usually, in the case that the temperature becomes higher than the optimum range, an amount of an oxidized decomposition product such as acetic acid, carbon monoxide or carbon dioxide is increased and consequently, the yield is lowered. Although an oxidation reaction in which a target product is produced is an exothermic reaction and accompanies a large heat release, the heat of reaction of these side reactions is still larger and when a rate of the side reactions becomes large, the overall heat of reaction becomes still larger. Further, because a reaction rate increases exponentially with a temperature, the side reactions may cause a runaway reaction. Therefore, when an oxidation reaction is performed in a fixed-bed multitubular reactor, it is required to define exactly a quality of a catalyst, a method of packing the catalyst or an operating condition to prevent the temperature from exceeding the optimum condition.

For example, a method for improving a temperature distribution in a reaction tube is being proposed as disclosed in Japanese Patent Application, First Publication No. Hei 6-192144.

In this literature, when producing methacrolein from isobutylene or tertiary butyl alcohol and molecular oxygen as raw materials by a gas-phase catalytic oxidation reaction, a method in which a catalyst powder supported on a carrier inactive to the reaction is used as the catalyst and a supported amount of the catalyst powder is increased gradually from an inlet part to an outlet part of a reaction tube by dividing a longitudinal direction of the reaction tube into a plurality of sections is disclosed.

Further, a method of promoting a removal of heat by increasing a circulating amount of a heat medium outside a reaction tube and a method of monitoring precisely the temperature in a reaction tube and the other methods are proposed as a method for performing a gas-phase catalytic oxidation reaction stably.

For example, Japanese Patent Application, First Publication No. 2001-139499 discloses a method of circulating a heat medium into a shell side of a reactor through a circulating devise in a fixed-bed multitubular reactor and suppressing an increase in a temperature in a reaction tube, wherein a part of a heat medium drawn out of the shell side of the reactor is heat exchanged and the heat-exchanged heat medium is returned to the shell side of the reactor, thereby controlling a temperature difference between the heat medium drawn out and the one introduced in at a range from 15 to 150° C.

Further, Japanese Patent Application, First Publication No. Hei 8-92147 discloses a method of suppressing a temperature of a catalyst layer, wherein when propylene is oxidized to acrolein with a gas-phase catalytic oxidation by using a fixed-bed multitubular reactor equipped with a heat-medium bath, a flow rate of the heat-medium is controlled so that a temperature of the heat-medium bath is raised to the extent of 2 to 10° C. in the course of the time that the heat medium is introduced in the heat-medium bath through the inlet part of the heat medium and moved to reach the outlet part of the heat medium.

Furthermore, as a method of measuring a temperature of the longitudinal direction of a reaction tube, for example, as disclosed in Japanese Patent Application, First Publication No. 2002-212127, a method of measuring the temperature of the longitudinal direction in the reaction tube, wherein some of the reaction tubes which represent the whole fixed-bed multitubular reactor are provided with protecting tubes before packing catalysts, into which thermocouples are inserted is exemplified.

However, any concrete methods to operate an adequately stable gas-phase catalytic oxidation reaction were not disclosed in the methods described in Japanese Patent Application, First Publication No. Hei 6-192144. That is, a concrete method for changing an activity or a concrete length of each section of a reaction tube to realize an operation for a stable reaction were not disclosed. Furthermore, in Japanese Patent Application, First Publication No. Hei 6-192144, an absolute value of the maximum value of ΔT (hereinafter, referred to as ΔT max or a hotspot part) in the first and the second sections was not disclosed and, in addition, because a difference between the ΔT max of the first and the second sections was large, it was difficult to perform an adequately stable operation.

Further, as a method described in Japanese Patent Application, First Publication No. 2001-139499 or Japanese Patent Application, First Publication No. Hei 8-92147, it is important for a stable and high-efficiency operation to maintain the optimum condition through monitoring a temperature of a catalyst layer, but in these literatures, only a method of measuring a quantity or a temperature of a heat medium which was flowed in a reactor shell side was disclosed and a technology to measure the temperature of the catalyst layer precisely was not disclosed. As a result, a position of ΔT max was not identified sufficiently and the reaction conditions were not maintained adequately stably.

Further, a method described in Japanese Patent Application, First Publication No. 2002-212127 was able to easily measure the temperatures of various positions in the longitudinal direction of a catalyst layer, however, it was too complicated to be practical for a commercial use in a fixed-bed multitubular reactor. That is, the fixed-bed multitubular reactor of an industrial scale mostly has hundreds to thousands of reaction tubes, and in many cases it has tens of thousands, and moreover, the length of the reaction tube is several meters, so that it was difficult to understand and control the temperature of the catalyst layer in all of the reaction tubes because the number of thermocouples was too large.

Further, a temperature was sometimes measured by selecting several reaction tubes out of a plurality of reaction tubes and inserting thermocouples into the selected reaction tubes, however, because measuring positions were not determined, it was insufficient to understand a position of the maximum temperature ($\Delta T$ max) in the longitudinal direction of the catalyst layer, which is most important for a stable operation.

The present invention has been achieved taking the above-mentioned circumstances into consideration and has an object to provide a fixed-bed multitubular reactor in which an oxidation reaction can be operated stably under the optimum condition with a supreme level by measuring a temperature distribution precisely and practically in the longitudinal direction of a reaction tube packed with a catalyst of the fixed-bed multitubular reactor and understanding a position of a hotspot part.

DISCLOSURE OF INVENTION

The present invention provides a fixed-bed multitubular reactor, comprising:

a plurality of reaction tubes to be packed with a catalyst; and catalyst temperature measurers equipped to measure the temperature near the center part in the radial direction of the reaction tubes, the catalyst temperature measurers being installed in each of a part or all of the plurality of the reaction tubes, the measurement positions thereof being different from each other in the longitudinal direction of the reaction tubes.

In the fixed-bed multitubular reactor of the present invention, it is preferable that the catalyst temperature measurers are equipped in 5 to 35 tubes out of a reaction tube group comprising 5 to 109 reaction tubes adjacent each other.

In the fixed-bed multitubular reactor of the present invention, it is preferable that a plurality of the reaction tube groups is provided and distributed in the portion where a flow pattern of a heat medium flowing outside the reaction tube is different.

In the fixed-bed multitubular reactor of the present invention, it is preferable that the reactor is for a gas-phase catalytic oxidation reaction.

In the fixed-bed multitubular reactor of the present invention, it is preferable that the gas-phase catalytic oxidation reaction is a reaction synthesizing an unsaturated aldehyde or an unsaturated carboxylic acid from propylene, isobutylene or tertiary butyl alcohol.

In the fixed-bed multitubular reactor of the present invention, it is preferable that the gas-phase catalytic oxidation reaction is a reaction synthesizing an unsaturated carboxylic acid from an unsaturated aldehyde.

Using the fixed-bed multitubular reactor of the present invention, an oxidation reaction can be operated stably under the optimum condition with a supreme level by measuring a temperature distribution precisely and practically in the longitudinal direction of a reaction tube packed with a catalyst of the fixed-bed multitubular reactor and understanding a position of a hotspot part.

BEST MODE FOR CARRING OUT THE INVENTION

An example of a fixed-bed multitubular reactor of the present invention is explained by referring to the figures.

Figure 1:
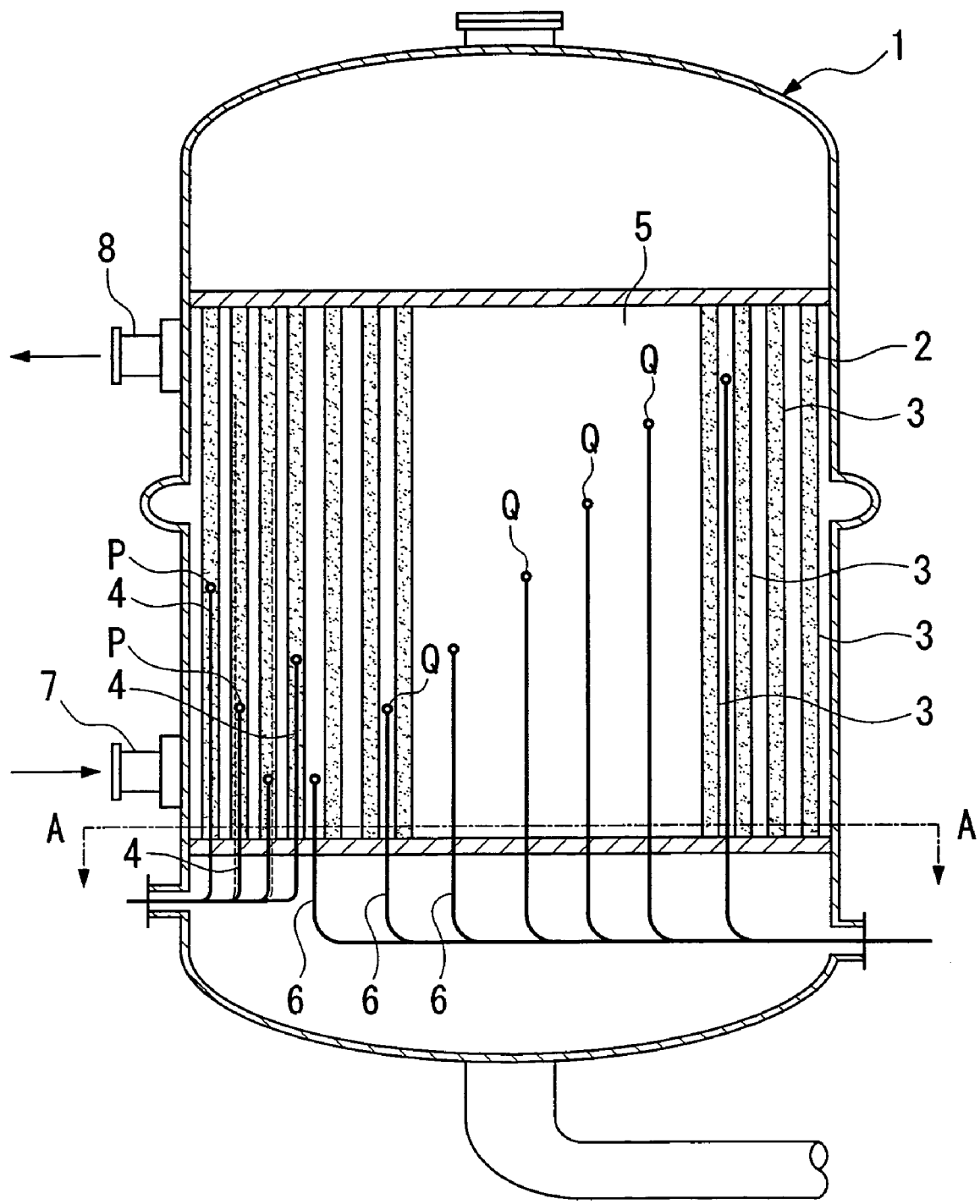
FIG. 1 is a schematic diagram showing an example of a constitution of a fixed-bed multitubular reactor of the present invention.

FIG. 1 is a schematic diagram showing a constitution of a fixed-bed multitubular reactor. The fixed-bed multitubular reactor 1 is a reactor in which a gas-phase catalytic oxidation reaction is performed, comprising roughly: a plurality of reaction tubes 3 packed with a catalyst and forming a catalyst layer 2; catalyst temperature measurers 4 being inserted in each of not all but a part of the plurality of the reaction tubes 3; a heat-medium bath 5 located outside the reaction tubes 3; and heat-medium bath temperature measurers 6 measuring temperatures of the heat-medium 5.

In this fixed-bed multitubular reactor 1, measurement positions P of the catalyst temperature measurers 4 inserted in the plurality of the reaction tubes 3 are different from each other in the longitudinal direction of the reaction tubes and not uniformly fixed.

Figure 2:
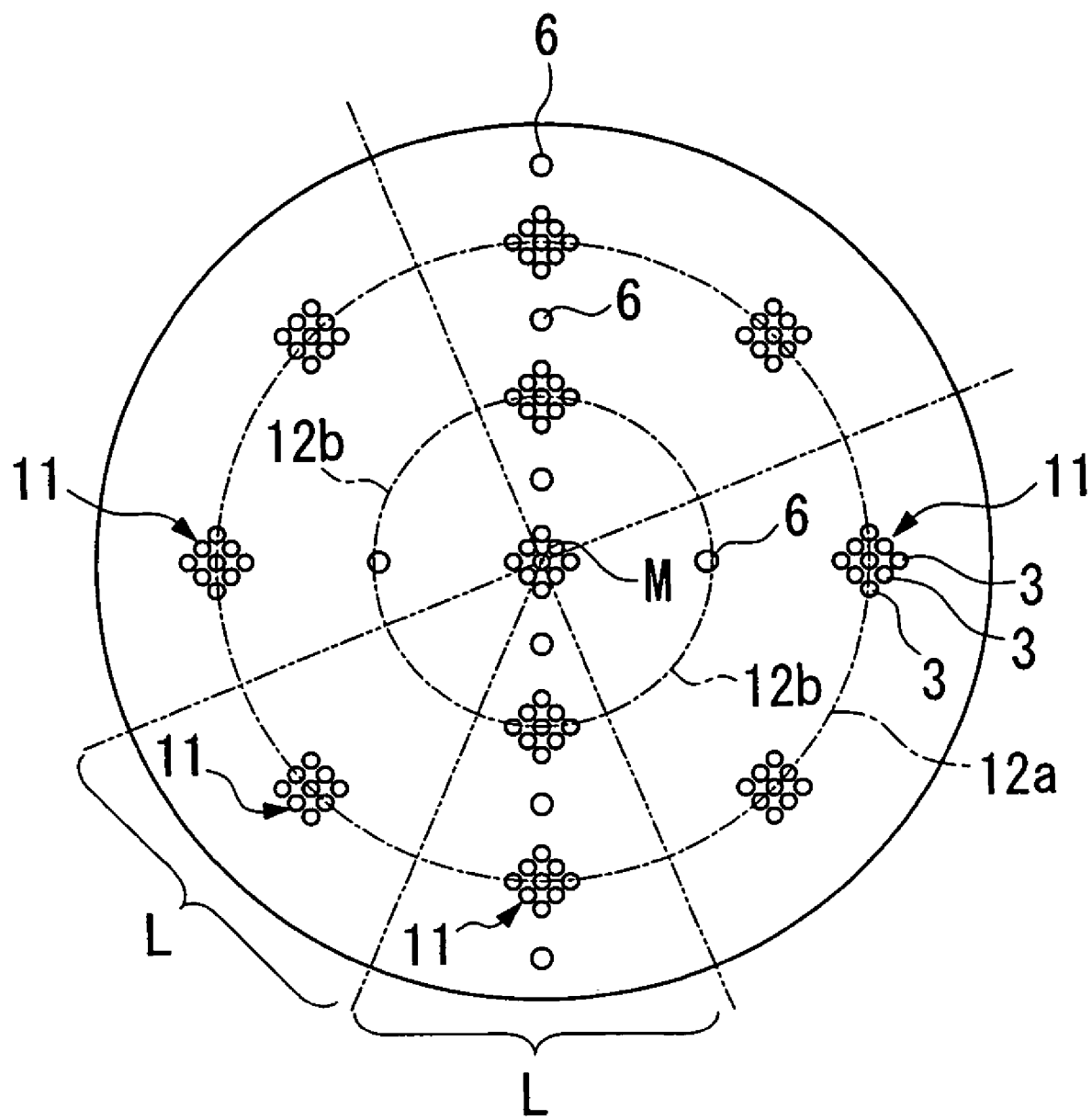
FIG. 2 is a schematic diagram of a cross section of the fixed-bed multitubular reactor along the line of A-A in FIG. 1.

Further, the plurality of the reaction tubes 3 is arranged so as to be adjacent to each other to form a reaction tube group 11 as shown in FIG. 2. Here, it is preferable that at least a part of the reaction tubes forming the reaction tube group 11 are equipped with the catalyst temperature measurers.

As mentioned above, when the reaction tubes 3 are forming the reaction tube group 11 and at least a part of the reaction tube group 11 is equipped with the catalyst temperature measurers, it is possible to understand a temperature distribution of the catalyst layer with high precision. And the term "be adjacent to" means that the pitch of the arrangement of the reaction tubes is within a range of the fifth tube from a standard tube. However, the range is different depending on the total number of the reaction tubes and becomes small in case the total number of the reaction tubes decreases. Further, in case the pitch of the arrangement of the reaction tubes exceeds the range of the fifth tube, there is a risk of a decrease in the precision of the temperature measurement because the number of the reaction tubes increases.

In the case that at least a part of the reaction tube group 11 are equipped with the catalyst temperature measurers, it is preferable that the catalyst temperature measurers are equipped in 5 to 35 tubes out of the reaction tube group comprising 5 to 109 reaction tubes adjacent to each other.

Figure 3:
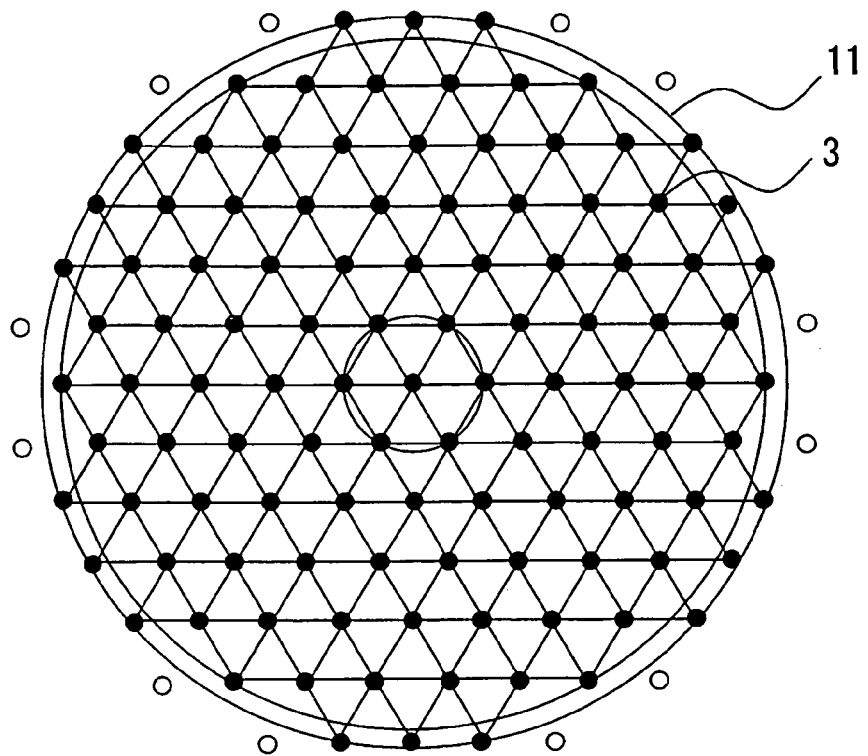
FIG. 3 is a diagram showing a reaction tube group in the case that reaction tubes are arranged in a triangular configuration.
Figure 4:
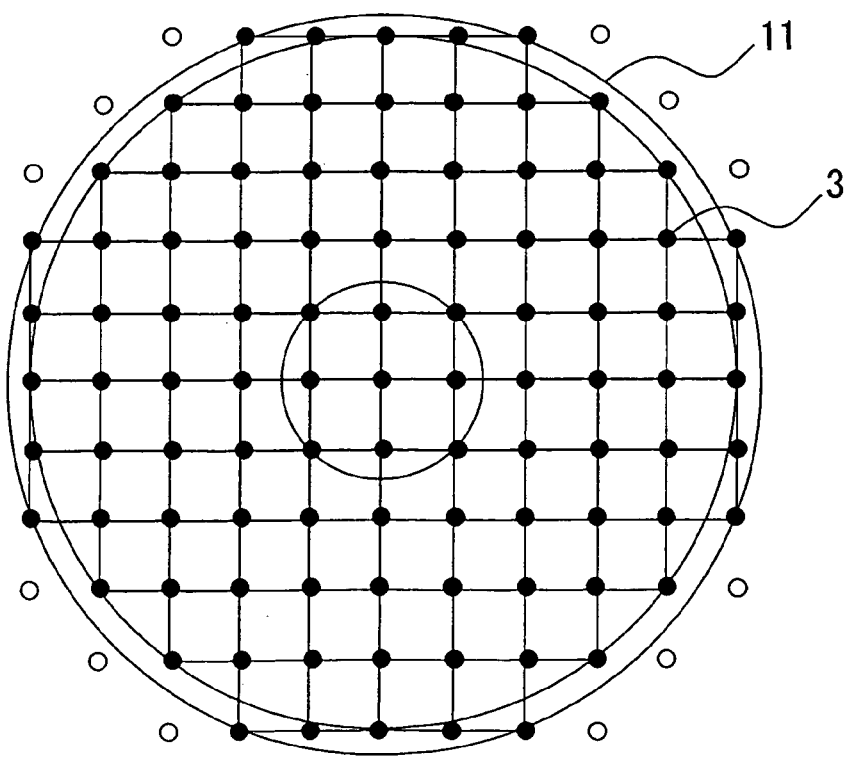
FIG. 4 is a diagram showing a reaction tube group in the case that reaction tubes are arranged in a square configuration.

The reason that the number of the reaction tubes in the reaction tube group is 5 to 109 is explained below. In a multitubular reactor, reaction tubes are usually arranged in a triangular configuration as shown in FIG. 3 or in a square configuration as shown in FIG. 4. In FIG. 3 and FIG. 4, the reaction tubes are arranged at intersections (black points) of each straight line.

When the reaction tube group 11 is constituted with the reaction tubes, the pitch of the arrangement of which is within a range of the about fifth tube from a standard central reaction tube (within the outermost circle in the Figure), the number of the reaction tubes constituting the reaction tube group is 109 in the case of the triangular configuration and 97 in the case of the square configuration. Further, when the reaction tube group is constituted with the reaction tubes, the pitch of the arrangement of which is within a range of the first tube from a standard central reaction tube (within the innermost circle in the Figure), the number of the reaction tubes constituting the reaction tube group is 7 in the case of the triangular configuration and 5 in the case of the square configuration. Consequently, the maximum number and the minimum number in the reaction tube group are 109 and 5, respectively.

In addition, in the case that the number of the reaction tubes equipped with catalyst temperature measurers is less than 5, a temperature distribution in the catalyst layer may not be well understood, and in the case the number exceeds 35, equipment accompanying the installment of the catalyst temperature measurers becomes large.

Further, in the case that the total number of the reaction tubes is less than 35, the number of the reaction tubes equipped with the catalyst temperature measurers is inevitably less than the total number of the reaction tubes.

Furthermore, the reaction tubes equipped with the catalyst temperature measurers are preferably located within a range of the first tube from and adjacent to a standard reaction tube, because the temperature distribution of the longitudinal direction of the reaction tubes can be understood more precisely.

Moreover, in the case that the catalysts with different activities are packed in a reaction tube, preferably at least one or more preferably two catalyst temperature measurers are equipped in each catalyst section.

In the case that a plurality of the reaction tube groups is provided, it is preferable that these reaction tube groups are distributed at a place where a flow pattern of a heat medium flowing outside the reaction tube is different.

Figure 5:
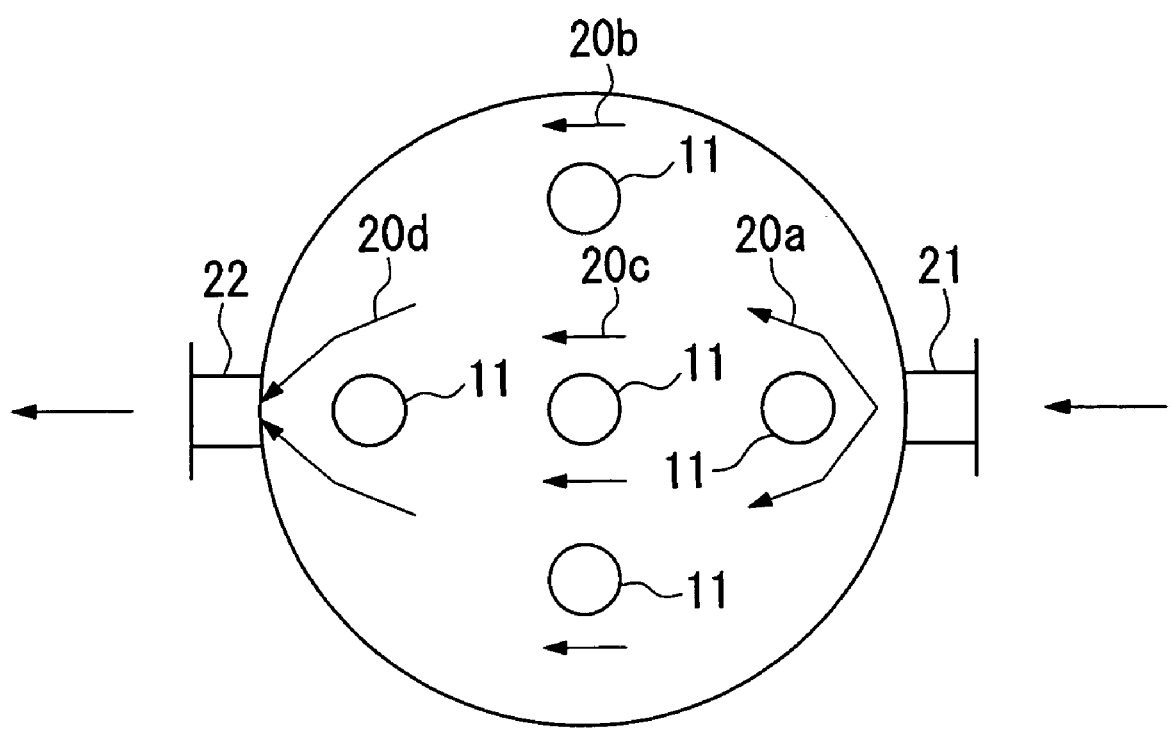
FIG. 5 is a diagram explaining a flow pattern of a heat medium.

Here, a flow pattern of a heat medium is explained. The flow pattern of the heat medium means a fluid state of the heat medium (a rate of flow, a direction of flow: illustratively shown as arrows 20-a, 20-b, 20-c, 20-d in FIG. 5) when looking at a cross section which is a section of a fixed-bed multitubular reactor cut at a rectangular direction to a longitudinal direction of the reaction tube (hereinafter abbreviated as a cross section; refer to FIG. 5). Usually, the reactor is designed so as to make the flow pattern of the heat medium become homogeneous, and the inlet 21 and the outlet 22 of the heat medium, for example, are provided pointing opposite directions to each other or pointing the same direction as shown in FIG. 5. However, it is difficult to make the flow pattern of the heat medium totally identical and there exists a place where the flow of the heat medium is easy or difficult in the fixed-bed multitubular reactor. Especially, when the number of the reaction tubes is large, a difference of the flow pattern of the heat medium in the fixed-bed multitubular reactor tends to become large. The difference of the flow pattern causes a change in heat transfer state in the reaction tube so that temperatures of the reaction tubes contacting the heat medium of different flow patterns are liable to be different from one another.

Consequently, in the case that a plurality of the reaction tube groups 11 are allocated to the portions where the flow patterns 20-a, 20-b, 20-c and 20-d of the heat medium flowing outside the reaction tubes of each reaction tube groups are different, it is possible to understand the temperature in the fixed-bed multitubular reactor more precisely.

Further, as an arrangement of the reaction tube groups in the case there exists a plurality of the reaction tube groups, it is preferable that a plurality of the reaction tube groups 11 are allocated circularly (on the circles 12-a and 12-b in FIG. 2) and at least one reaction tube group 11 is allocated in each section L which is made by separating the cross section of the reactor in the radial direction from the center M into two or more sections having the same area.

By monitoring the temperature of the catalyst layer in the fixed-bed multitubular reactor in this manner, it is possible to monitor the temperature of a hotspot part in an operation accompanying a large heat generation such as in an oxidation reaction. By controlling the reaction based on the measured results, a gas-phase catalytic oxidation reaction can be operated stably with high efficiency.

In the fixed-bed multitubular reactor described above, it is preferable that a plurality of the heat-medium bath temperature measurers 6 is equipped corresponding to the catalyst temperature measurers 4 so that the measurement positions Q thereof are set at the same height as the measurement positions P of the catalyst temperature measurers 4 (positions in the longitudinal direction of the reaction tube), as shown in FIG. 1. Further, in case that the measurement positions Q of the heat-medium bath temperature measurers 6 are set at the same height as the measurement positions P of the catalyst temperature measurers 4 (positions in the longitudinal direction of the reaction tube), a $\Delta T$ of each position can be obtained precisely even in the case that there occurs a certain inhomogeneous temperature distribution of the heat medium in the heat-medium bath 5 caused by a shape of the reactor, a reaction condition or a fluid state of the heat medium.

The number of the reaction tubes of the fixed-bed multitubular reactor 1 is not particularly limited. The number is from several tens to, in an ordinary case, the upper limit of several thousands or several tens of thousands determined depending on mechanical restrictions on the manufacturing of the multitubular reactor. The length of the reaction tube is not particularly limited either, but it is generally from around 1 to 10 meters. In the case that the length of the reaction tube is short, the number of the reaction tubes is increased so that unevenness of the packing, the activity or the rate of heat removal by the heat medium in each reaction tube is liable to occur. On the other hand, in the case that the length of the reaction tube is long, a pressure drop becomes large and a power for supplying gases is increased. Further, generally, the selectivity to a target product tends to decrease when a reaction pressure is high, so that taking these into consideration, the length of the reaction tube is preferably from around 2 to 7 meters.

Furthermore, the internal diameter of the reaction tube 3 is usually from 20 to 30 mm.

In addition, in the fixed-bed multitubular reactor, the raw gas of the reaction may be supplied from the bottom to the top or the other way into the reaction tube 3.

The catalyst to be packed in the reaction tube 3 is not particularly limited as far as it is a solid oxidation catalyst and a conventionally known catalyst in accordance with a reaction can be used, which includes a solid oxidation catalyst such as a composite oxide containing molybdenum. Specifically, a catalyst in which 10 to 400 parts by mass of a metal oxide catalyst such as molybdenum and bismuth is supported on 100 parts by mass of an inactive carrier such as a porous carrier of silica or alumina can be exemplified, as disclosed in Japanese Patent Application, First Publication No. Hei 6-192144.

The method for preparing such a catalyst is not particularly limited and various conventionally well-known methods can be adopted. A raw material to be used for a catalyst preparation is not particularly limited and a nitrate, a carbonate, an acetate, an ammonium salt, an oxide, a halide and the like of each element can be used in combination.

The catalyst temperature measurers 4 and the heat-medium bath temperature measurers 6 equipped in the fixed-bed multitubular reactor are not particularly limited as far as they can be used industrially and a thermocouple or a resistance thermometer is generally used. Further, such a temperature measurer is preferably inserted into a protecting tube because a certain degree of mechanical strength is necessary.

Furthermore, the setting interval of the catalyst temperature measurers 4 is preferably from 0.1 to 2 meters, more preferably from 0.5 to 1 meter. In case the interval is too narrow, the number of the heat-medium bath temperature measurers 6 measuring the whole fixed-bed multitubular reactor 1 is increased so that there is a risk not only of increasing the cost of the equipment but also of obstructing the flow of the heat-medium. Further, in case the interval is too wide, it is difficult to measure the temperature distribution precisely so that it may be difficult to understand the position or the temperature of a hotspot part.

The heat-medium to be filled up in the heat-medium bath 5 is not particularly limited and a fused-salt of potassium nitrate and sodium nitrite, an organic heat medium such as Dowtherm system, or the like is generally used.

Further, the fixed-bed multitubular reactor 1 is generally equipped with temperature detecting elements (not shown in the Figure) at the inlet 7 and the outlet 8 of the heat-medium bath so that the reaction temperature is controlled with the inlet temperature.

Generally, a baffle can be inserted in the shell side (the heat-medium bath 5 side) of the fixed-bed multitubular reactor 1 so as to control the flow of the heat medium. When the baffle is inserted, it is preferable that at least one heat-medium bath temperature measurers 6 is provided in each section separated with the baffle.

Further, it is preferable that at least one heat-medium bath temperature measurers 6 is provided in each place where the direction of the heat-medium flow is different in the heat-medium bath 5.

The gauge pressure of the outlet of the reaction tube is 100 to 1000 kPa; the reaction temperature is 200 to 500° C.; the concentration of the raw material to be oxidized in the raw gas of the reaction is 1 to 10%; the molar ratio of oxygen to the raw material to be oxidized in the raw gas of the reaction is 0.5 to 20; and the space velocity (SV) of the raw gas of the reaction is around 500 to 3000 h$^{-1}$ (NTP).

In the gas-phase catalytic oxidation reaction performed in such a fixed-bed multitubular reactor 1, a material to be oxidized and a oxidizing material are contained in the raw gas. The kind of such material is selected in accordance with a target product and as the material to be oxidized, for example, propylene, isobutylene, tertiary butyl alcohol, acrolein, methacrolein and the like are exemplified. And as the oxidizing material, molecular oxygen or water vapor is used. As a source of molecular oxygen, air is preferably used from the economic point of view, but oxygen enriched air may be used as occasion demands.

The raw gas may contain a small amount of impurity such as lower saturated aldehyde and the like as far as it doesn't practically have an effect on the reaction, or may be diluted by adding an inert gas such as nitrogen, water vapor, carbon dioxide or the like. The composition ratio of each component of the raw gas is determined in view of the productivity of the target product and the explosion range.

The present invention is especially effective in a reaction synthesizing an unsaturated aldehyde or an unsaturated carboxylic acid from propylene, isobutylene or tertiary butyl alcohol and/or a reaction synthesizing an unsaturated carboxylic acid from an unsaturated aldehyde among the gas-phase catalytic oxidation reactions.

EXAMPLES

In the following Examples, an example of a catalytic oxidation reaction of methacrolein is shown as a gas-phase catalytic oxidation reaction and a publicly well-known catalyst of phosphorous-molybdenum-vanadium system was used as an oxidation catalyst the composition of which was obtained from a charged amount of the raw material of the catalyst component ("part" in the following description represents "part by mass"). As a heat-medium of the fixed-bed multitubular reactor, a fused-salt composed of 50% by mass of potassium nitrate and 50% by mass of sodium nitrite was used. And the raw materials and the products of the oxidation reaction were analyzed with gas chromatography.

Experimental Example 1

In 300 parts of pure water, 100 parts of ammonium paramolybdate, 2.8 parts of ammonium methavanadate and 9.2 parts of cesium nitrate were dissolved and an aqueous solution was obtained. To the aqueous solution, a solution obtained by dissolving 8.2 parts of 85 mass % phosphoric acid in 10 parts of pure water and a solution obtained by dissolving 1.1 parts of telluric acid in 10 parts of pure water were added while stirring and heated to 95° C. Then, a solution obtained by dissolving 3.4 parts of copper nitrate, 7.6 parts of ferric nitrate, 1.4 parts of zinc nitrate and 1.8 parts of magnesium nitrate in 80 parts of pure water was added. Further, the mixed solution was stirred at 100° C. for 15 minutes and a slurry was obtained.

Then the obtained slurry was dried and 2 parts of graphite was added and mixed to 100 parts of the dried material, and molded by a tableting machine into a ring shaped tablet which has an external diameter of 5 mm, an internal diameter of 2 mm and a length of 3 mm. And the resultant tablet was calcined under airflow at 380° C. for 5 hours and a catalyst (1) was obtained. The atomic composition of the catalyst (1) is represented in the Table 1.

TABLE 1

| Atom | Composition (molar %) |
| --- | --- |
| Mo | 12 |
| P | 1.5 |
| Cu | 0.3 |
| V | 0.5 |
| Fe | 0.4 |
| Te | 0.1 |
| Mg | 0.15 |
| Zn | 0.1 |
| Cs | 1.0 |

In the gas-phase catalytic oxidation reaction of this Example, a steel fixed-bed multitubular reactor equipped with a heat-medium bath (the reaction tubes were arranged in a triangular configuration and an internal diameter of each reaction tube was 25.4 mm) was used. In the fixed-bed multitubular reactor, a reaction tube groups in which 31 reaction tubes inserted with thermocouples (catalyst temperature measurers) from the inlet side of the raw gas were concentrated being adjacent to each other were allocated to each section which is made by separating the cross section of the reactor in the radial direction from the center into 4 sections having the same area. The thermocouples were inserted in each reaction tube in such a way that the measurement position was shifted by 10 cm along the longitudinal direction of the reaction tube (in the lengthwise direction of the catalyst layer). As for each reaction tube group, the distance from the center and the interval between each reaction tube group were made equal when viewing the cross section.

Further, the thermocouples for measuring the temperature of the heat-medium bath (the heat-medium bath temperature measurers) were arranged with the same intervals corresponding to the catalyst temperature measurers and further arranged at the inlet side and the outlet side of the heat medium.

To the inlet side of the raw gas of the reaction tubes equipped with such temperature measurers, a mixture comprising 370 ml of the catalyst (1) and 130 ml of spherical alumina having an external diameter of 5 mm was packed and to the outlet side of the raw gas, only 1000 ml of the catalyst (1) was packed. The resultant length of the catalyst layer was 3000 mm.

Then a raw gas comprising 5.5% by volume of methacrolein, 10.7% by volume of oxygen, 9.0% by volume of water vapor and 74.8% by volume of nitrogen was introduced into the catalyst layer at a space velocity of 630 $hr^{-1}$ and a gas phase catalytic oxidation reaction was carried out with a flow method under atmospheric pressure.

The temperatures of the catalyst layer and the heat-medium bath side were measured at this time by the equipped thermocouples (the catalyst-temperature measurer, the heat-medium temperature measurer) with 10 cm intervals in the longitudinal direction of the reaction tube and consequently, it became clear that the $\Delta T$ near the outlet of the raw gas in the catalyst layer was in the range from 18° C. to 23° C. and the $\Delta T$ in the vicinity of the middle of the catalyst layer was in the range from 15° C. to 20° C. and the $\Delta T$ near the inlet of the raw gas was in the range from 20° C. to 30° C. Further, concretely, it was recognized that a hotspot part ($\Delta T=30°$ C.) was formed at a position 800 mm from the inlet of the raw gas in the catalyst layer.

In addition, the other reaction tube groups were entirely measured in the same manner, and as a result, nearly the same $\Delta T$ distribution and a position of the hotspot part were shown and the $\Delta T$ distribution of the whole fixed-bed multitubular reactor could be understood. Consequently, a stable startup could be realized because of the understanding of the $\Delta T$ distribution of the whole fixed-bed multitubular reactor. Further, a hotspot part ($\Delta T=40°$ C.) was formed at a position 600 mm from the inlet of the raw gas in the catalyst layer by the subsequent load-up, and the movement of the hotspot was recognized easily because the catalyst layer temperature was measured with 10 cm intervals in the longitudinal direction of the reaction tube.

Experimental Example 2

The reaction was carried out in the same manner as in Experimental Example 1 except that the heat-medium bath temperature measurers were equipped only at the inlet and the outlet of the heat-medium bath and only one catalyst temperature measurer was equipped at a position 800 mm from the inlet of the raw gas in the reaction tube near the center of the fixed-bed multitubular reactor. As a result, $\Delta T=30°$ C. was recognized at the position 800 mm from the inlet of the raw gas, but the position of the hotpot part was not clear so that a runaway reaction of the catalyst was brought about and the temperature control became impossible and the reaction was compelled to stop.

Experimental Example 3

The reaction was carried out in the same manner as in Experimental Example 1 except that 1500 ml of the catalyst (1) was packed without dilution. As a result, the $\Delta T$ near the outlet of the raw gas in the catalyst layer was in the range from 15° C. to 20° C. and the $\Delta T$ in the vicinity of the middle of the catalyst layer was in the range from 20° C. to 25° C. and the $\Delta T$ near the inlet of the raw gas was in the range from 30° C. to 40° C. Further, concretely, it was recognized that a hotspot part ($\Delta T=40°$ C.) was formed at a position 400 mm from the inlet of the raw gas in the catalyst layer. In addition, the other reaction tube groups showed similar values and the $\Delta T$ distribution of the whole reactor was recognized regardless of the packing condition of the catalyst and it was known that a stable startup can be realized.

Experimental Example 4

The reaction was carried out in the same manner as in Experimental Example 1 except that catalyst tube groups in which 4 reaction tubes inserted with thermocouples with a 100 cm interval in the longitudinal direction from the inlet of the raw gas of the catalyst layer were concentrated being adjacent to each other were distributed at the center of the fixed-bed multitubular reactor and at one position on a circle having the same center. As a result, the $\Delta T$ near the outlet of the raw gas in the catalyst layer was in the range from 15° C. to 16° C. and the $\Delta T$ in the vicinity of the middle of the catalyst layer was in the range from 18° C. to 20° C. and the $\Delta T$ near the inlet of the raw gas was in the range from 20° C. to 22° C. and the difference of $\Delta T$ could be recognized. However, the position of the hotspot part could not be recognized precisely and it took a long time to reach the operation of a normal reaction load and the productivity was a little lowered to maintain a stable operation.

Experimental Example 5

The reaction was carried out in the same manner as in Experimental Example 3 except that a plurality of the reaction tubes inserted with the thermocouples were not arranged adjacent to each other in one reaction tube group, and the thermocouples were equipped in 10 reaction tubes at random. As a result, the temperature distribution of the catalyst layer in the longitudinal direction was not clearly understood and the position of the hotspot part was not clear. As for the result of the reaction, the selectivity to methacrylic acid was around 2% lower as compared with Experimental Example 3. The operation was able to be continued for 1000 hours, but in a part of the reaction tubes, the catalyst with a trace of experiencing a runaway reaction was recognized when the catalyst was recovered after the reaction was finished.

As mentioned above, the preferable embodiments of the present invention have been explained, however the present invention is not limited to the embodiments thereof. It is possible to add, omit or substitute a constitution or to make other changes as far as it doesn't deviate from the scope of the present invention. The present invention is not limited by the foregoing explanation, but is limited only by the scope of the attached claims.

INDUSTRIAL APPLICABILITY

The present invention relates to a fixed-bed multitubular reactor, comprising:
- a plurality of reaction tubes filled with a catalyst; and
- catalyst temperature measurers equipped to measure the temperature near the center part in the radial direction of the reaction tubes, the catalyst temperature measurers being installed in each of a part or all of the plurality of the reaction tubes, the measurement positions thereof being different from each other in the longitudinal direction of the reaction tubes.

Using the fixed-bed multitubular reactor of the present invention, an oxidation reaction can be operated stably under the optimum condition with a supreme level by measuring a temperature distribution precisely and practically in the longitudinal direction of a reaction tube packed with a catalyst of the fixed-bed multitubular reactor and understanding a position of a hotspot part.

The invention claimed is:

1. A fixed-bed multitubular reactor, comprising:
   a plurality of reaction tubes to be packed with a catalyst;
   catalyst temperature measures equipped to measure the temperature near the centre part in the radial direction of the reaction tubes;
   a heat-medium bath located outside of said reaction tubes;
   heat-medium bath temperature measures measuring temperatures of said heat-medium;
   at least a portion of said plurality of reaction tubes being arranged so as to be adjacent to each other to form at least one reaction tube group;
   wherein the catalyst temperature measures being installed in all of the plurality of the reaction tubes or at least a part of said reaction tubes forming said at least one reaction tube group, the measurement positions thereof being different from each other in the longitudinal direction of the reaction tubes; and
   the heat-medium bath temperature measures are equipped corresponding to the catalyst temperature measures so that the measurement positions Q thereof are set at the same height as the measurement positions P of the catalyst temperature measures.

2. The fixed-bed multitubular reactor according to claim 1, wherein the catalyst temperature measurers are equipped in 5 to 35 tubes out of a reaction tube group comprising 5 to 105 reaction tubes adjacent to each other.

3. The fixed-bed multitubular reactor according to claim 2, wherein flow patterns of a heat medium are different in the reactor, and a plurality of the reaction tube groups are provided and respectively allocated to the positions where the flow patterns of the heat medium are different.

4. A method for conducting a gas-phase catalytic oxidation reaction, comprising:
   oxidizing a gas in the fixed-bed multitubular reactor of claim 1.

5. The method according to claim 4, wherein the gas-phase catalytic oxidation reaction is a reaction synthesizing an unsaturated aldehyde or an unsaturated carboxylic acid from propylene, isobutylene or tertiary butyl alcohol.

6. The method according to claim 4, wherein the gas-phase catalytic oxidation reaction is a reaction synthesizing an unsaturated carboxylic acid from an unsaturated aldehyde.

7. The fixed-bed multitubular reactor according to claim 1, wherein a plurality of the reaction tubes groups are allocated circularly and at least one reaction tube group is allocated in each section L which is made by separating the cross section of the reactor in the radial direction from the centre M into two or more sections having the same area.

8. The fixed-bed multitubular reactor according to claim 1, wherein the length of the reaction tube is 2 to 7 meters.

9. The fixed-bed multitubular reactor according to claim 1, wherein the setting interval of the catalyst temperature measures is from 0.1 to 2 meters.

10. The fixed-bed multitubular reactor according to claim 1, comprising a plurality of reaction tube groups arranged in a triangular configuration.

11. The fixed-bed multitubular reactor according to claim 1, comprising a plurality of reaction tube groups arranged in a square configuration.

* * * * *